(12) United States Patent
McBride et al.

(10) Patent No.: US 7,699,203 B2
(45) Date of Patent: Apr. 20, 2010

(54) VARIABLE ANGLE SURGICAL STAPLE INSERTER

(75) Inventors: Larry T. McBride, Memphis, TN (US); Robert B. Rice, Southaven, MS (US)

(73) Assignee: Warsaw Orthopedic, Inc.

( * ) Notice: Subject to any disclaimer, the term of this patent is extended or adjusted under 35 U.S.C. 154(b) by 124 days.

(21) Appl. No.: 11/559,118

(22) Filed: Nov. 13, 2006

(65) Prior Publication Data

US 2008/0110957 A1 May 15, 2008

(51) Int. Cl.
*A61B 17/068* (2006.01)
(52) U.S. Cl. ...................... 227/175.1; 227/19
(58) Field of Classification Search ... 227/175.1–182.1, 227/19; 81/44; 606/104, 216, 219; 294/19.1
See application file for complete search history.

(56) References Cited

U.S. PATENT DOCUMENTS

| | | | |
|---|---|---|---|
| 337,212 A * | 3/1886 | Van Dusen | 81/44 |
| 696,390 A | 3/1902 | Chamberlin | |
| 1,000,903 A | 8/1911 | Elia | |
| 2,889,170 A * | 6/1959 | Bode | 294/86.32 |
| 3,200,884 A * | 8/1965 | Solum et al. | 166/241.6 |
| 3,527,492 A * | 9/1970 | Hollis | 294/19.1 |
| 3,604,487 A * | 9/1971 | Gilbert | 81/443 |
| 3,605,123 A | 9/1971 | Hahn | |
| 3,606,862 A * | 9/1971 | Huff | 118/306 |
| 3,855,638 A | 12/1974 | Pilliar | |
| 4,437,191 A | 3/1984 | van der Zel et al. | |
| 4,438,769 A * | 3/1984 | Pratt et al. | 227/175.1 |
| 4,476,590 A | 10/1984 | Scales et al. | |
| 4,536,894 A | 8/1985 | Galante et al. | |
| 4,542,539 A | 9/1985 | Rowe, Jr. et al. | |
| 4,576,167 A | 3/1986 | Noiles | |
| 4,594,786 A * | 6/1986 | Rezmer | 33/506 |
| 4,599,085 A | 7/1986 | Riess et al. | |
| 4,646,745 A | 3/1987 | Noiles | |
| 4,854,496 A | 8/1989 | Bugle | |
| 4,969,591 A | 11/1990 | Richards et al. | |
| 5,084,050 A | 1/1992 | Draenert | |
| 5,094,618 A | 3/1992 | Sullivan | |
| 5,098,434 A | 3/1992 | Serbousek | |
| 5,119,983 A | 6/1992 | Green et al. | |
| 5,120,171 A | 6/1992 | Lasner | |
| 5,158,222 A | 10/1992 | Green et al. | |
| 5,181,645 A | 1/1993 | Matsutani et al. | |
| 5,205,459 A | 4/1993 | Brinkerhoff et al. | |
| 5,226,766 A | 7/1993 | Lasner | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,312,024 A | 5/1994 | Grant et al. | |

(Continued)

*Primary Examiner*—Rinaldi I. Rada
*Assistant Examiner*—Lindsay Low (57) ABSTRACT

A surgical staple inserter is disclosed and can include a shaft and a staple engagement arm pivotably engaged with the shaft. Further, the surgical staple inserter can include a spring that can be connected to the shaft and the staple engagement arm. The surgical staple inserter can be moved between a straight position and a bent position. In the straight position, the staple engagement arm can be substantially aligned with the shaft. In the bent position, the staple engagement arm can be rotated with respect to the shaft.

22 Claims, 11 Drawing Sheets

U.S. PATENT DOCUMENTS

| | | | |
|---|---|---|---|
| 5,329,834 A * | 7/1994 | Wong | 81/58.3 |
| 5,360,448 A | 11/1994 | Thramann | |
| 5,360,452 A | 11/1994 | Engelhardt et al. | |
| 5,368,593 A | 11/1994 | Stark | |
| 5,380,325 A | 1/1995 | Lahille et al. | |
| 5,381,943 A | 1/1995 | Allen et al. | |
| 5,392,979 A | 2/1995 | Green et al. | |
| 5,405,073 A | 4/1995 | Porter | |
| 5,417,533 A | 5/1995 | Lasner | |
| 5,425,490 A * | 6/1995 | Goble et al. | 227/175.1 |
| 5,431,323 A | 7/1995 | Smith et al. | |
| 5,458,143 A * | 10/1995 | Herr | 135/68 |
| 5,465,894 A | 11/1995 | Clark et al. | |
| 5,476,206 A | 12/1995 | Green et al. | |
| 5,478,003 A | 12/1995 | Green et al. | |
| 5,492,442 A | 2/1996 | Lasner | |
| 5,505,736 A | 4/1996 | Reimels et al. | |
| 5,516,288 A | 5/1996 | Sichler et al. | |
| 5,560,634 A * | 10/1996 | Challande et al. | 280/634 |
| 5,562,682 A | 10/1996 | Oberlin et al. | |
| 5,564,615 A | 10/1996 | Bishop et al. | |
| 5,577,654 A | 11/1996 | Bishop | |
| 5,588,580 A | 12/1996 | Paul et al. | |
| 5,588,581 A | 12/1996 | Conlon et al. | |
| 5,601,224 A | 2/1997 | Bishop et al. | |
| 5,667,513 A * | 9/1997 | Torrie et al. | 606/104 |
| 5,797,918 A * | 8/1998 | McGuire et al. | 606/104 |
| 5,844,356 A * | 12/1998 | Peters et al. | 313/481 |
| 5,896,630 A * | 4/1999 | Smith et al. | 24/600.1 |
| 5,904,689 A * | 5/1999 | Jonjic | 606/99 |
| 6,209,638 B1 | 4/2001 | Mikolajczyk | 166/241.1 |
| 6,484,803 B1 | 11/2002 | Gremillion | 166/241.6 |
| 6,539,677 B1 * | 4/2003 | Lanka | 52/127.2 |
| 6,718,601 B1 * | 4/2004 | Choate | 24/600.2 |
| 6,767,356 B2 * | 7/2004 | Kanner et al. | 606/213 |
| 6,860,889 B2 * | 3/2005 | Bonati et al. | 606/104 |
| 6,875,237 B2 * | 4/2005 | Dye | 623/22.21 |
| 6,964,363 B2 | 11/2005 | Wales et al. | |
| 6,969,474 B2 | 11/2005 | Beaty | |
| 6,981,628 B2 | 1/2006 | Wales | |
| 6,984,235 B2 | 1/2006 | Huebner | |
| 7,048,541 B2 | 5/2006 | Hall et al. | |
| 7,063,701 B2 | 6/2006 | Michelson | |
| 7,063,702 B2 | 6/2006 | Michelson | |
| 7,074,221 B2 | 7/2006 | Michelson | |
| 7,094,239 B1 | 8/2006 | Michelson | |
| 7,175,648 B2 * | 2/2007 | Nakao | 606/220 |
| 7,255,703 B2 * | 8/2007 | Mujwid et al. | 606/104 |
| 2001/0000903 A1 | 5/2001 | Heck et al. | |
| 2001/0021853 A1* | 9/2001 | Heckele et al. | 606/99 |
| 2003/0028218 A1* | 2/2003 | Bauer | 606/213 |
| 2005/0154469 A1* | 7/2005 | Novelli | 623/19.11 |
| 2005/0260542 A1 | 11/2005 | Hall | |
| 2005/0283191 A1 | 12/2005 | Fontayne et al. | |
| 2006/0000869 A1 | 1/2006 | Fontayne | |
| 2006/0011698 A1 | 1/2006 | Okada et al. | |
| 2006/0058791 A1 | 3/2006 | Broman et al. | |
| 2006/0095040 A1 | 5/2006 | Schlienger et al. | |
| 2006/0097025 A1 | 5/2006 | Milliman et al. | |
| 2006/0106390 A1 | 5/2006 | Jensen et al. | |
| 2006/0121080 A1 | 6/2006 | Lye et al. | |
| 2006/0149255 A1 | 7/2006 | Doubler et al. | |
| 2006/0149263 A1 | 7/2006 | Newcomb et al. | |
| 2006/0163312 A1 | 7/2006 | Viola et al. | |
| 2006/0190080 A1 | 8/2006 | Danoff et al. | |
| 2006/0193886 A1 | 8/2006 | Owens et al. | |
| 2006/0193887 A1 | 8/2006 | Owens et al. | |
| 2006/0193888 A1 | 8/2006 | Lye et al. | |
| 2006/0193889 A1 | 8/2006 | Spradlin et al. | |
| 2007/0005077 A1* | 1/2007 | Null et al. | 606/104 |
| 2007/0138120 A1* | 6/2007 | Anderson et al. | 213/75 R |

* cited by examiner

VARIABLE ANGLE SURGICAL STAPLE INSERTER

FIELD OF THE DISCLOSURE

The present disclosure relates generally to surgical staples. More specifically, the present disclosure relates to devices for inserting surgical staples into tissue.

BACKGROUND

Surgical staples can be used to close surgical wounds and other wounds. Further, surgical staples can be used to treat certain spinal deformities, such as scoliosis. Some surgical staples can be made from shape memory metal alloys. A surgical staple made from a shape memory metal alloy can be deformed from an original shape and installed in a patient. Then, heat can be applied to the surgical staple to return the deformed staple to the original shape. Depending on the location of the tissue into which the staple is inserted, it can be difficult to properly orient the staple with respect to the tissue and drive the staple into the tissue.

Accordingly, there is a need for a staple inserter that can be used to install surgical staples in areas within a patient that are relatively difficult to access.

DETAILED DESCRIPTION OF THE DRAWINGS

A surgical staple inserter is disclosed and can include a shaft and a staple engagement arm pivotably attached to the shaft. The staple engagement arm can be configured to engage an inserter engagement hole in a surgical staple.

In another embodiment, a method of inserting a surgical staple is disclosed and can include engaging a surgical staple inserter with a surgical staple. The surgical staple can be formed with an inserter engagement hole. Also, a staple engagement arm on the surgical staple inserter can extend at least partially through the surgical staple. The method can also include bending the surgical staple inserter in situ in order to align the surgical staple with a target area.

In yet another embodiment, a surgical staple inserter is disclosed and can include a shaft and a staple engagement arm pivotably engaged with the shaft. Further, the surgical staple inserter can include a spring that can be connected to the shaft and the staple engagement arm. The surgical staple inserter can be moved between a straight position and a bent position. In the straight position, the staple engagement arm can be substantially aligned with the shaft. In the bent position, the staple engagement arm can be rotated with respect to the shaft.

In still another embodiment, a surgical kit is disclosed and can include a surgical staple and a surgical staple inserter. The surgical staple can include a base and at least two tines can extend from the base. Also, an inserter engagement hole can be formed in the base. The surgical staple inserter can include a shaft and a staple engagement arm that can be pivotably attached to the shaft. The staple engagement arm can be configured to engage the inserter engagement hole formed in the base of the surgical staple.

Description of a Surgical Staple

Figure 1:
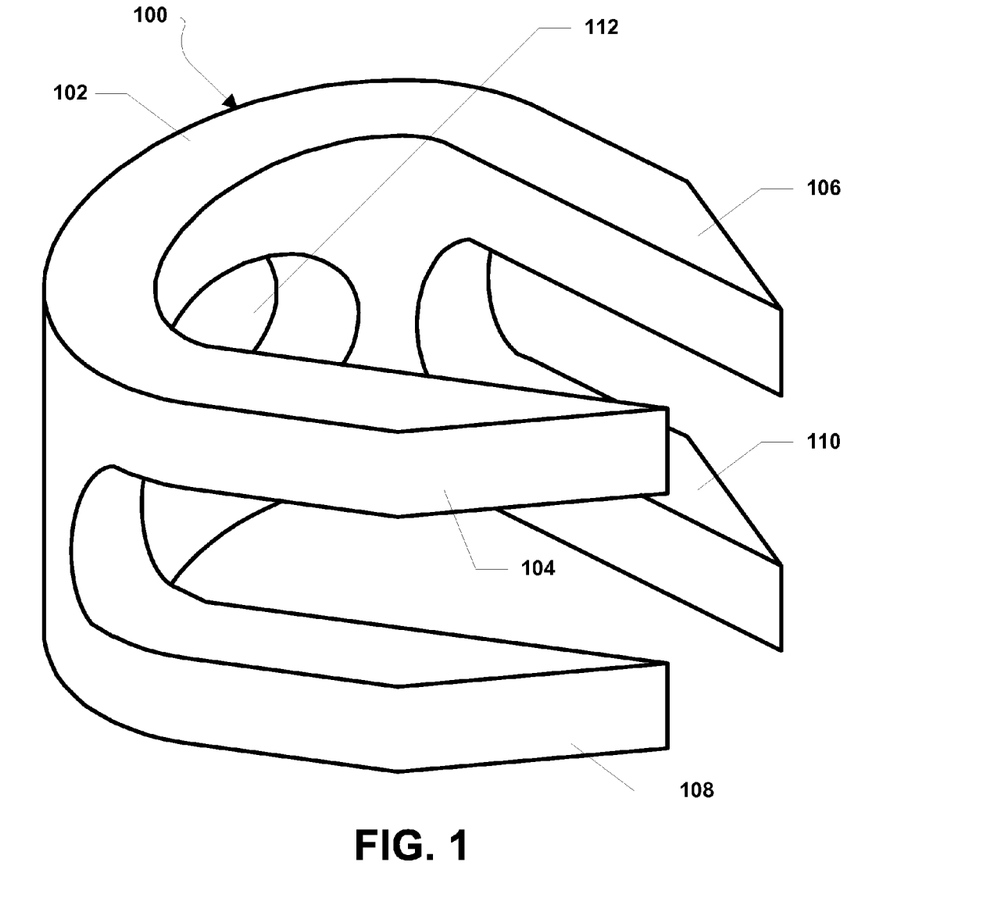
FIG. 1 is a perspective view of a surgical staple.
Figure 2:
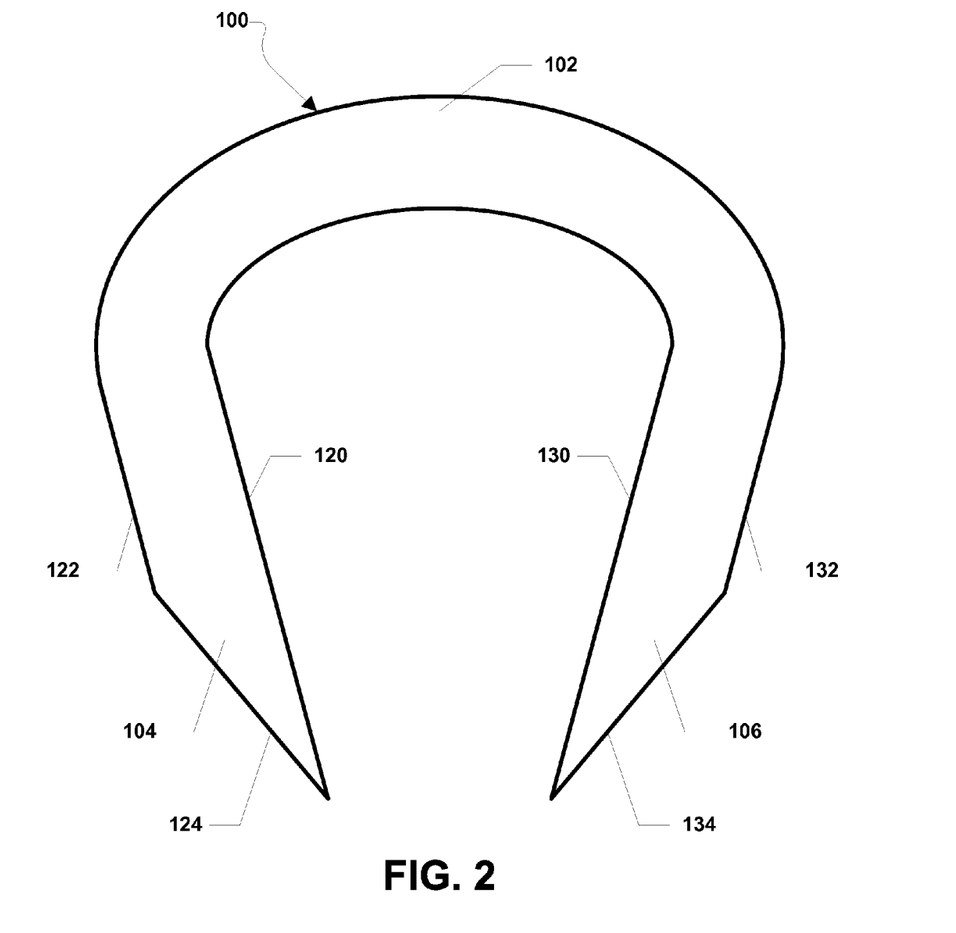
FIG. 2 is a top plan view of the surgical staple.
Figure 3:
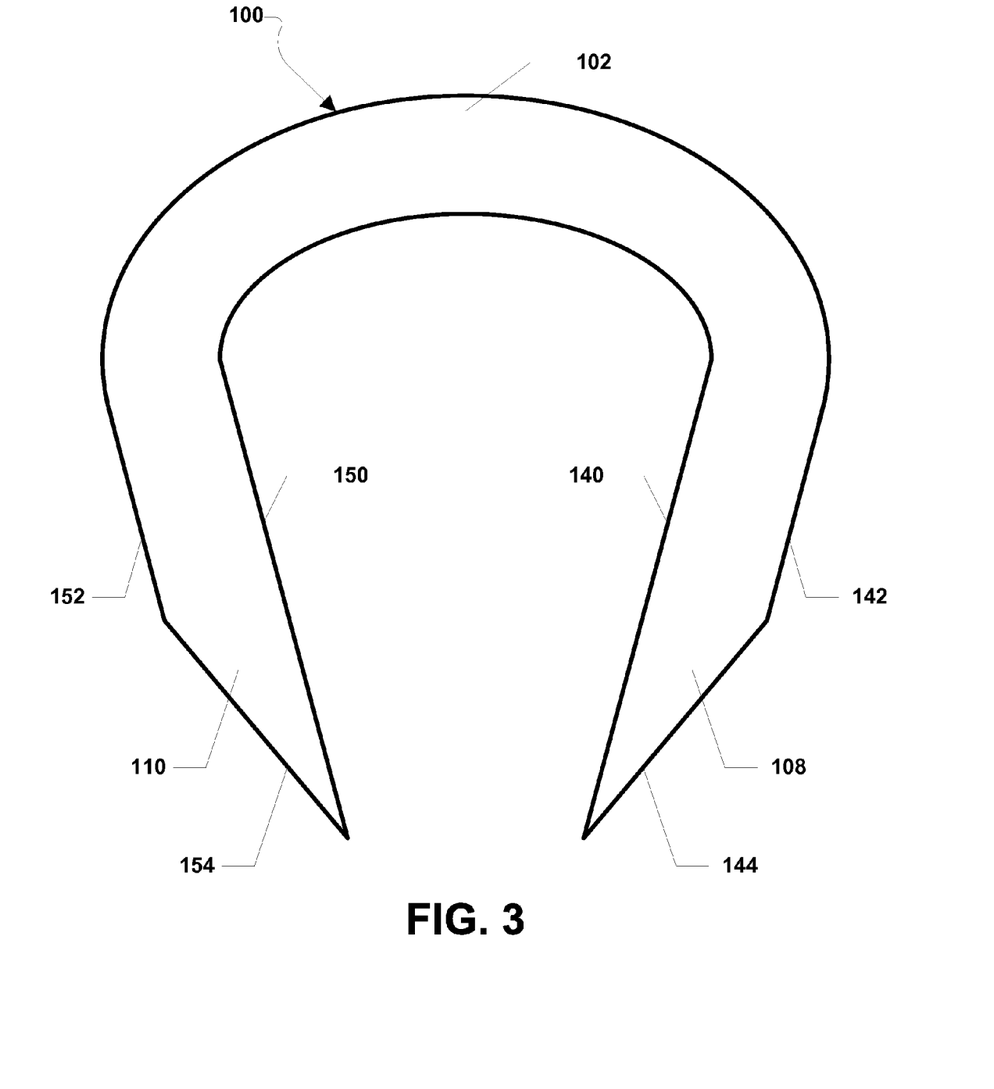
FIG. 3 is a bottom plan view of the surgical staple.

Referring to FIG. 1 through 3, a surgical staple 100 is shown. As shown, the surgical staple 100 can include a base 102. A first superior tine 104 and a second superior tine 106 can extend from the base 102. Further, a first inferior tine 108 and a second inferior tine 110 can extend from the base 102. In a particular embodiment, the first superior tine 104 can be substantially parallel to the first inferior tine 108. Also, the second superior tine 106 can be substantially parallel to the second inferior tine 110. FIG. 1 also shows that the surgical staple 100 can include an inserter engagement hole 112. The inserter engagement hole 112 can be configured to receive and removably engage a surgical staple inserter, e.g., the surgical staple inserter described herein.

As shown in FIG. 2, the first superior tine 104 can include an inner surface 120 and an outer surface 122. In a particular embodiment, the inner surface 120 of the first superior tine 104 can be longer than the outer surface 122 of the first superior tine 104. As such, the first superior tine 104 can include an angled portion 124 that extends from the inner surface 120 to the outer surface 122 and faces outward relative to the surgical staple 100. Alternatively, the outer surface 122 of the first superior tine 104 can be longer than the inner surface 120 of the first superior tine 104 and the angled portion 124 can extend from the inner surface 120 to the outer surface 122 and face inward relative to the surgical staple 100.

FIG. 2 further illustrates that the second superior tine 106 can also include an inner surface 130 and an outer surface 132. In a particular embodiment, the inner surface 130 of the second superior tine 106 can be longer than the outer surface 132 of the second superior tine 106. As such, the second superior tine 106 can include an angled portion 134 that extends from the inner surface 130 to the outer surface 132 and faces outward relative to the surgical staple 100. Alternatively, the outer surface 132 of the second superior tine 106 can be longer than the inner surface 130 of the second superior tine 106 and the angled portion 134 can extend from the inner surface 130 to the outer surface 132 and face inward relative to the surgical staple 100.

As depicted in FIG. 3, the first inferior tine 108 can include an inner surface 140 and an outer surface 142. In a particular embodiment, the inner surface 140 of the first inferior tine 108 can be longer than the outer surface 142 of the first inferior tine 108. As such, the first inferior tine 108 can include an angled portion 144 that extends from the inner surface 140 to the outer surface 142 and faces outward relative to the surgical staple 100. Alternatively, the outer surface 142 of the first inferior tine 108 can be longer than the inner surface 140 of the first inferior tine 108 and the angled portion 144 can extend from the inner surface 140 to the outer surface 142 and face inward relative to the surgical staple 100.

FIG. 3 also shows that the second inferior tine 110 can include an inner surface 150 and an outer surface 152. In a particular embodiment, the inner surface 150 of the second inferior tine 110 can be longer than the outer surface 152 of the second inferior tine 110. As such, the second inferior tine 110 can include an angled portion 154 that extends from the inner surface 150 to the outer surface 152 and faces outward relative to the surgical staple 100. Alternatively, the outer surface 152 of the second inferior tine 110 can be longer than the inner surface 150 of the second inferior tine 110 and the angled portion 154 can extend from the inner surface 150 to the outer surface 152 and face inward relative to the surgical staple 100.

In a particular embodiment, the surgical staple 100 can be inserted into tissue, e.g., flesh, bone, or a combination thereof, using a staple inserter. The staple inserter can be used to engage the surgical staple 100 and force the surgical staple 100 into the tissue. As the surgical staple 100 is driven into the tissue, the angled portion 124, 134, 144, 154 of each tine 104, 106, 108, 110 can move the tines 104, 106, 108, 110 in the direction of a memory shape associated with the surgical staple 100. For example, if the angled portion 124, 134, 144, 154 of each tine 104, 106, 108, 110 faces outward, the tines 104, 106, 108, 110 can bend inward as the surgical staple 100 is driven into the tissue. Alternatively, if the angled portion 124, 134, 144, 154 of each tine 104, 106, 108, 110 faces inward, the tines 104, 106, 108, 110 can bend outward as the surgical staple 100 is driven into the tissue. The initial bending of the tines 104, 106, 108, 110 can allow the surgical staple 100 to engage the tissue and prevent the surgical staple 100 from pulling out of the tissue as the staple inserter is disengaged from the surgical staple 100.

In a particular embodiment, after the surgical staple 100 is installed, the surgical staple 100 can be moved to a shape memory position, e.g., by applying heat to the surgical staple 100. The heat can be from an external source or from the body heat of the patient in which the surgical staple 100 is installed. In a particular embodiment, in the shape memory position, the tines 104, 106, 108, 110 of the surgical staple 100 can bend inward relative to the base 102 of the surgical staple 100. Alternatively, in the shape memory position, the tines 104, 106, 108, 110 of the surgical staple 100 can bend outward relative to the base 102 of the surgical staple 100.

Further, in a particular embodiment, the surgical staple 100 can be made from a biocompatible, shape memory metal alloy. For example, the surgical staple 100 can be made from a shape memory metal alloy of titanium and nickel, e.g., nitinol. Alternatively, the surgical staple 10 can be made from a biocompatible, shape memory polymer. Also, the surgical staple 100 can include any number of tines, e.g., two, three, four, etc.

Description of a Surgical Staple Inserter

Figure 4:
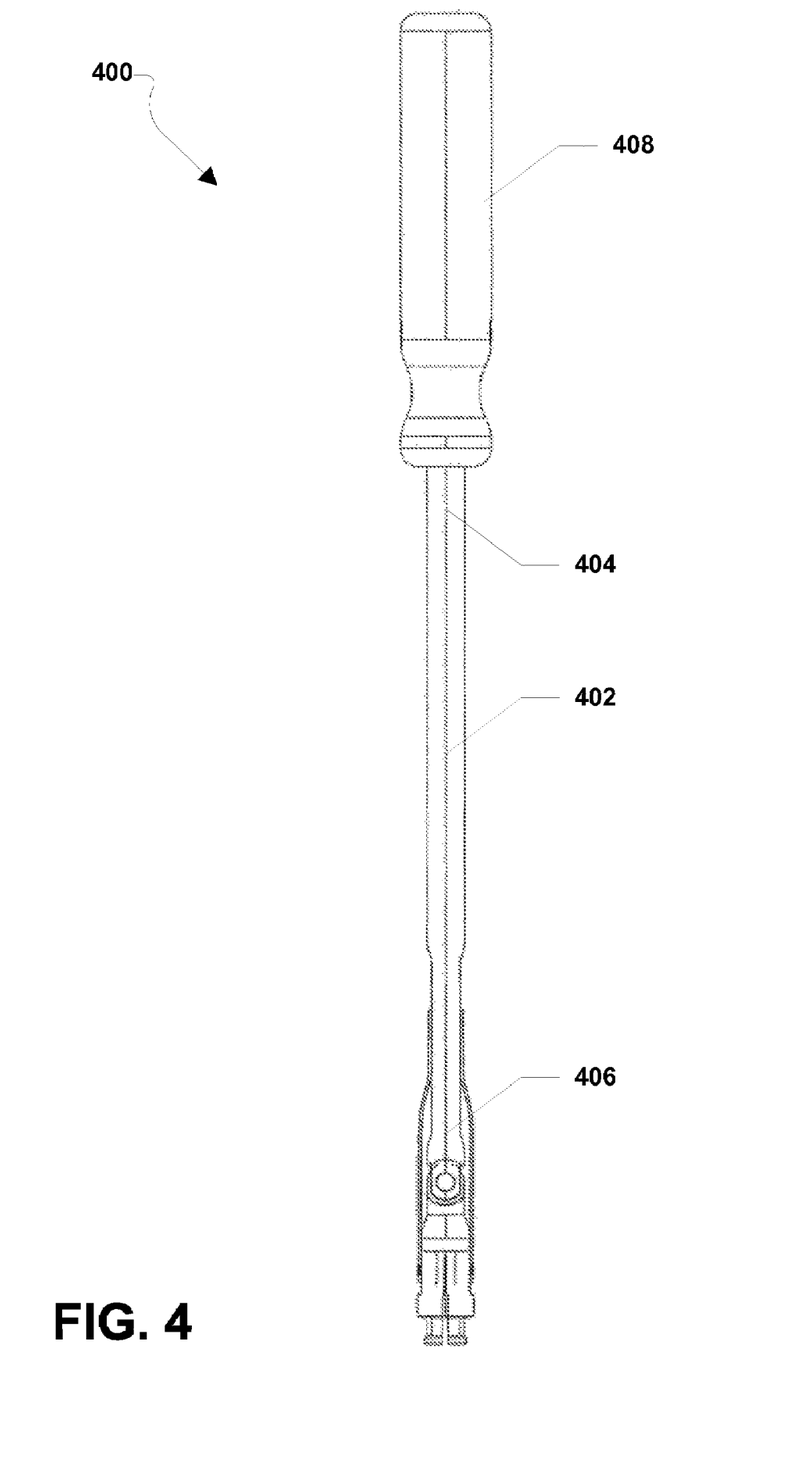
FIG. 4 is a plan view of a surgical staple inserter.
Figure 5:
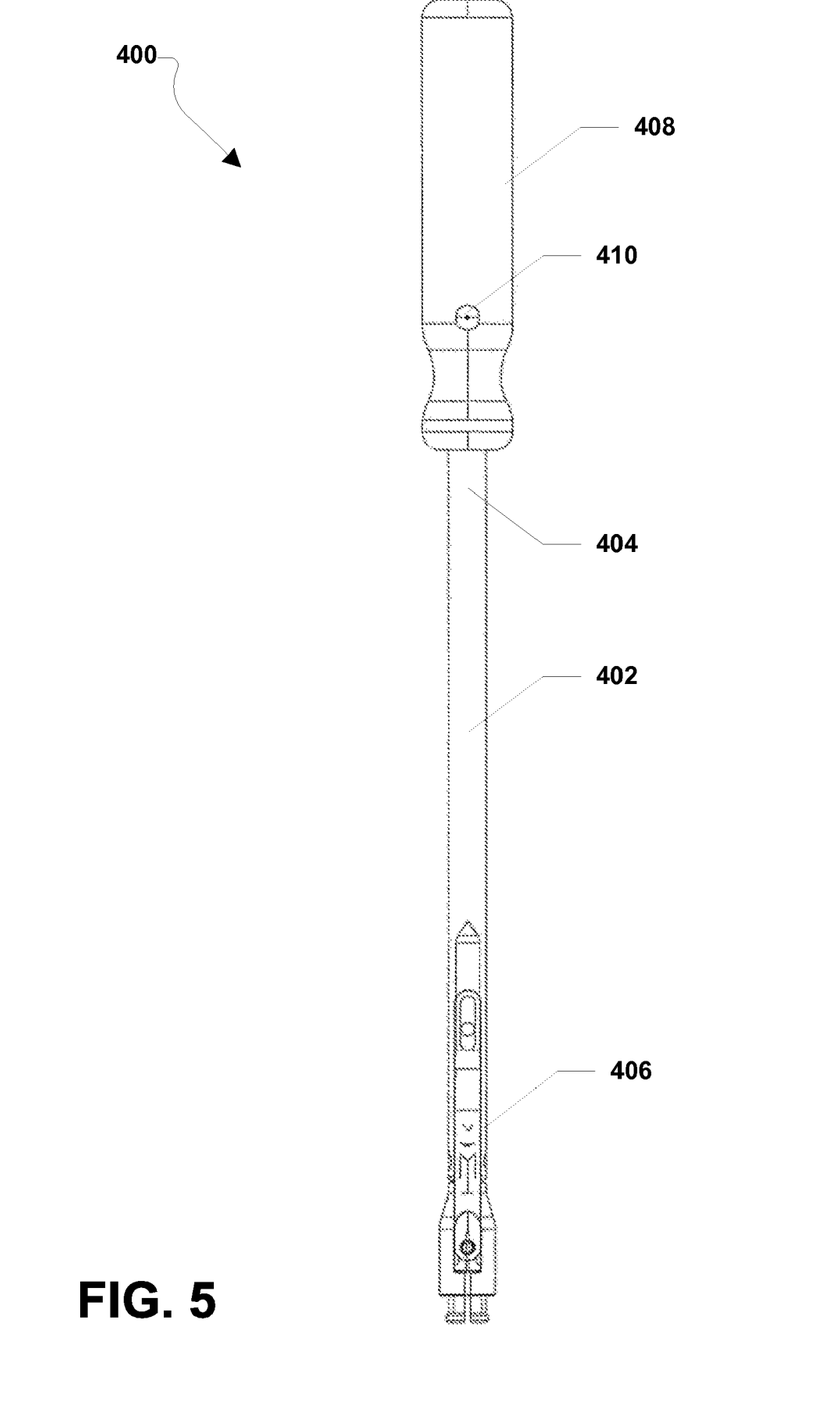
FIG. 5 is another plan view of the surgical staple inserter.

Referring to FIG. 4 through 10 a surgical staple inserter is shown and is generally designated 400. As illustrated in FIG. 4 and FIG. 5, the surgical staple inserter 400 can include a shaft 402 having a proximal end 404 and a distal end 406. A handle 408 can be engaged with the proximal end 404 of the shaft 402. In a particular embodiment, the handle 408 can be formed with an internal bore (not shown) and can be fitted over the proximal end 404 of the shaft 402. Further, the handle 408 can be held in place on the shaft 402 with a fastener 410, e.g., a bolt, screw, or similar device. Alternatively, the handle 408 can be integrally formed with the shaft 402. Moreover, the handle 408 can be press fitted onto the proximal end 404 of the shaft 402.

Figure 6:
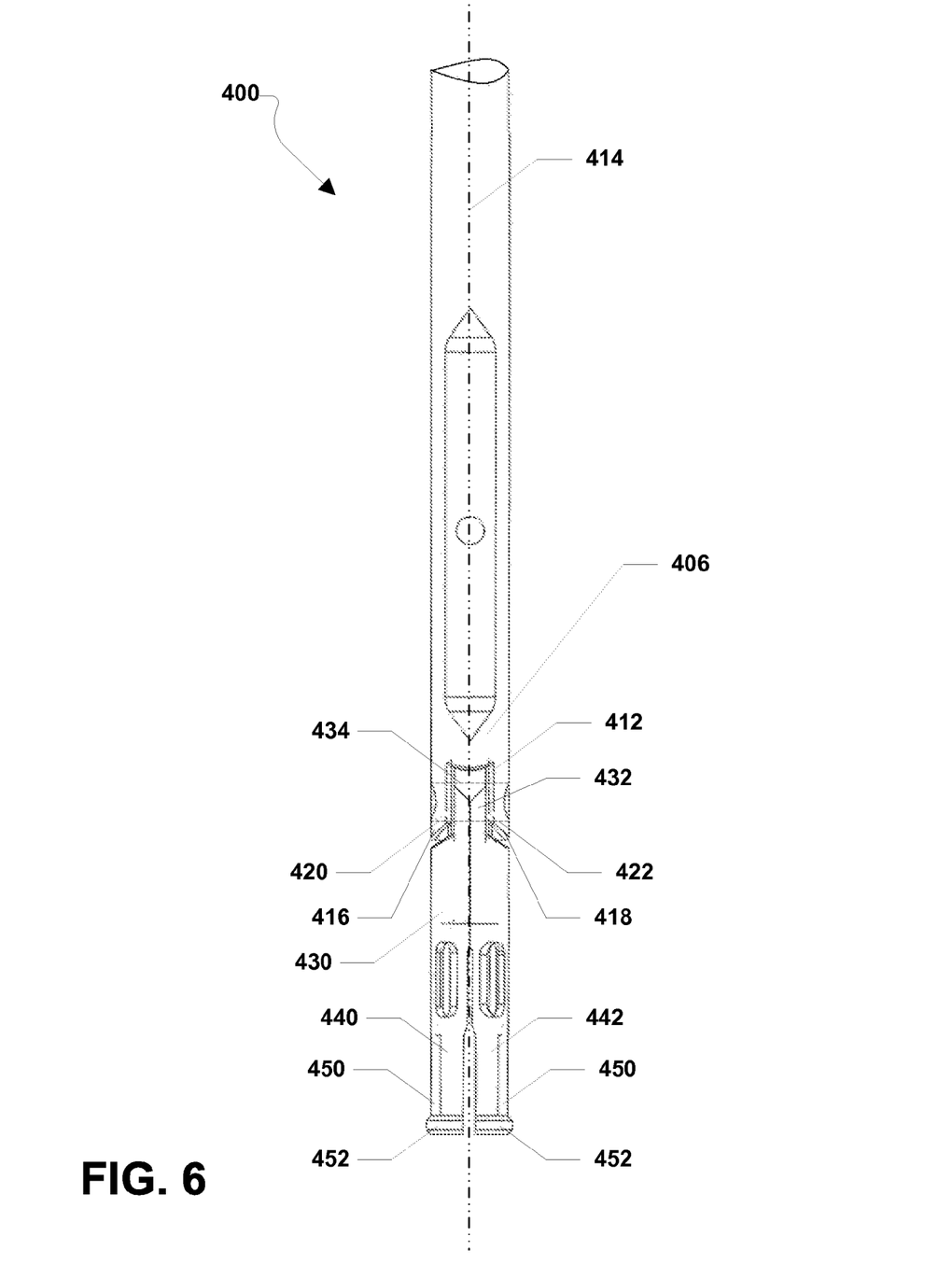
FIG. 6 is a detailed view of the surgical staple inserter with a first spring, a second spring, and a sleeve removed.

FIG. 6 shows that the distal end 406 of the shaft 402 can be formed with a groove 412. The groove 412 can be substantially parallel to a longitudinal axis 414 of the surgical staple inserter 400. The groove 412 can be flanked by a first distal end portion 416 and a second distal end portion 418. Each distal end portion 416, 418 can be formed with a hole 420, 422 that can be substantially perpendicular to the longitudinal axis 414 of the surgical staple inserter 400.

In a particular embodiment, a staple engagement arm 430 can be pivotably attached to the distal end 406 of the shaft 402. Specifically, as depicted in FIG. 6, the staple engagement arm 430 can include a tongue 432 extending there from. Particularly, the tongue 432 can extend from the staple engagement arm 430 in a direction that is substantially parallel to the longitudinal axis 414 of the surgical staple inserter 400. The tongue 432 can also be formed with a hole 434. The hole 434 can be substantially perpendicular to the tongue 432 and the longitudinal axis 414 of the surgical staple inserter 400.

When assembled, the tongue 432 of the staple engagement arm 430 can extend into the groove 412 formed in the distal end 406 of the shaft 402. A cylindrical member 436, e.g., a dowel, a post, a pin, or similar device, can be installed through the hole 420 in the first distal end portion 416 of the shaft 402, through the hole 434 in the tongue 432 of the staple engagement arm 430, and through the hole 422 in the second distal end portion 418 of the shaft 402. In a particular embodiment, the cylindrical member 436 can have a press fit engagement with the hole 420 in the first distal end portion 416 of the shaft 402 and the hole 422 in the second distal end portion 418 of the shaft 402. Further, the cylindrical member 436 can have a slip fit engagement with the hole 434 in the tongue 432 that extends from the staple engagement arm 430. Accordingly, the staple engagement arm 430 can pivot with respect to the shaft 402 around the cylindrical member 436.

Figure 7:
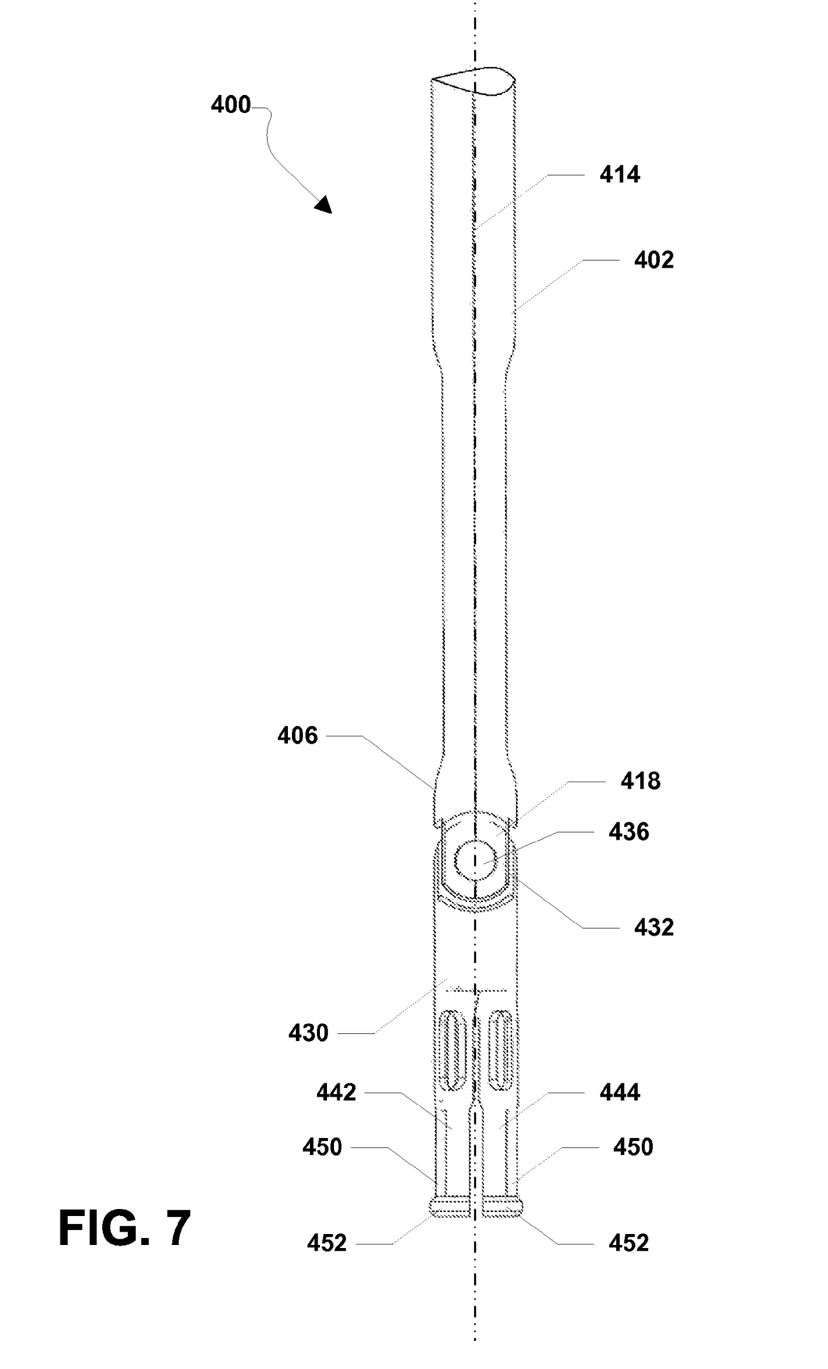
FIG. 7 is another detailed view of the surgical staple inserter with the first spring, the second spring, and the sleeve removed.
Figure 8:
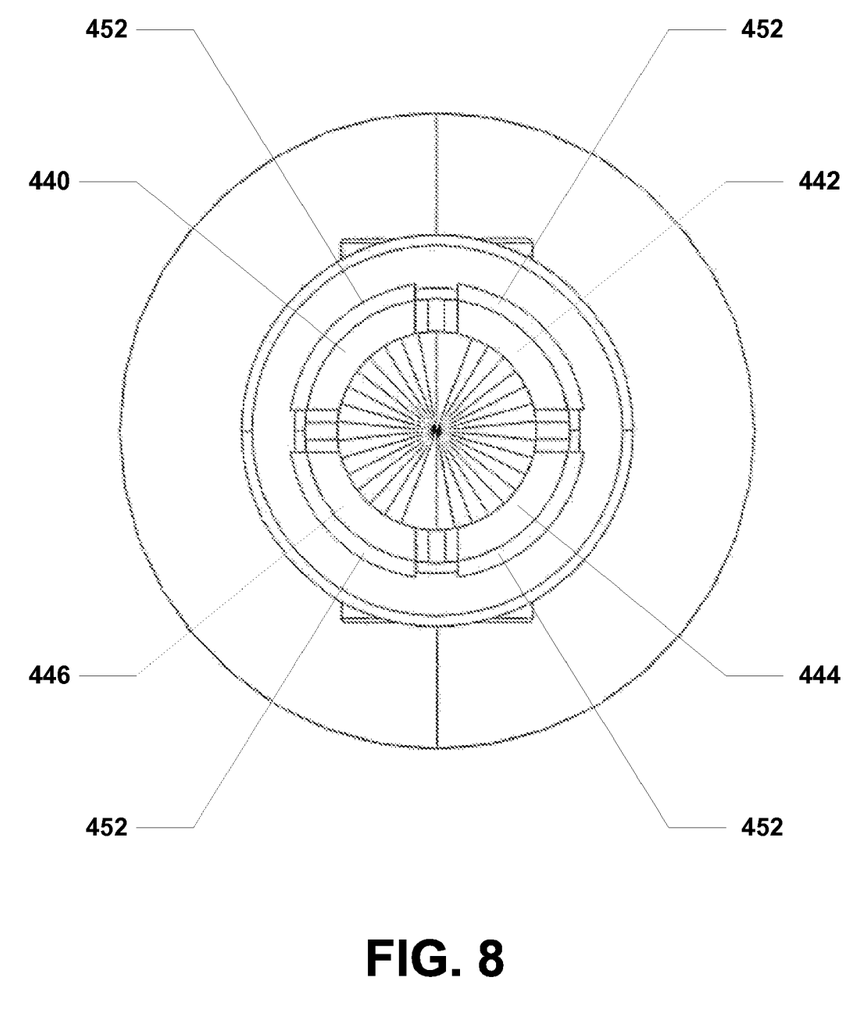
FIG. 8 is an end view of the surgical staple inserter.

FIG. 6 through FIG. 8 further indicate that the staple engagement arm 430 can include a first finger 440, a second finger 442, a third finger 444, and a fourth finger 446 extending there from. The fingers 440, 442, 444, 446 can extend from the staple engagement arm 430 in a direction that is substantially parallel to the longitudinal axis 414 of the surgical staple inserter 414 and in a direction that is substantially opposite the tongue 432 of the staple engagement arm. Each finger 440, 442, 444, 446 can include a distal end 450 and the distal end 450 of each finger 440, 442, 444, 446 can be formed with a protuberance 452.

During use, the surgical staple inserter 400 can be removably engaged with a surgical staple, e.g., the surgical staple described herein. Specifically, the fingers 440, 442, 444, 446 that extend from the surgical staple arm 430 of the surgical staple inserter 400 can be inserted into an inserter engagement hole of surgical staple. During insertion, the fingers 440, 442, 444, 446 can bend radially inward as the protuberance 452 on each finger 440, 442, 444, 446 slides against the leading edge and the inner periphery of the inserter engagement hole of the surgical staple. When the protuberance 452 on each finger 440, 442, 444, 446 clears the trailing edge of the inner periphery of the inserter engagement hole, the fingers 440, 442, 444, 446 can splay radially outward and return to a substantially straight position. The fingers 440, 442, 444, 446 can engage the inserter engagement hole in the surgical staple and the surgical staple can remain firmly attached to the staple engagement arm 430. Specifically, the protuberance 452 on each finger 440, 442, 444, 446 can hold the surgical staple on the surgical staple inserter 400 while the surgical staple is installed in a patient.

As the surgical staple is driven into a patient using the surgical staple inserter 400, the surgical staple can begin to move toward a shape memory position, e.g., due to the shaft of the tines. For example, as described above, the angle portion of each tine can cause each tine to bend inward or outward as the surgical staple is driven into the tissue. The bending of the tines can cause the surgical staple to engage the tissue and grip the tissue. Thereafter, the surgical staple inserter 400 can be removed from the surgical staple. Accordingly, the force of extracting the surgical staple inserter 400 from the surgical staple is substantially greater than the force of extracting the surgical staple from the tissue of the patient when the tines are bent during installation.

After the surgical staple inserter 400 is disengaged from the surgical staple, the surgical staple can be moved to a shape memory position, e.g., due to warming from the patient's body heat, due to the application of an external heat source, or due to another heat source. When the surgical staple is returned to the shape memory position within the patient, the surgical staple can be substantially bound in the patient.

As depicted in FIG. 4, FIG. 5, FIG. 9 and FIG. 10, the staple engagement arm 430 can further include a sleeve 460 disposed around the fingers 440, 442, 444, 446. A first spring 462 can be attached to the shaft 402 and the sleeve 460. Also, a second spring 464 can be attached to the shaft 402 and the sleeve 460. Each spring 462, 464 can include a proximal end 466 and a distal end 468. Further, the proximal end 466 of each spring 462, 464 can be formed with a slot 470 and the distal end 468 of each spring 462, 464 can be formed with a hole 472. As shown, each spring 462, 464 can be substantially flat.

Figure 9:
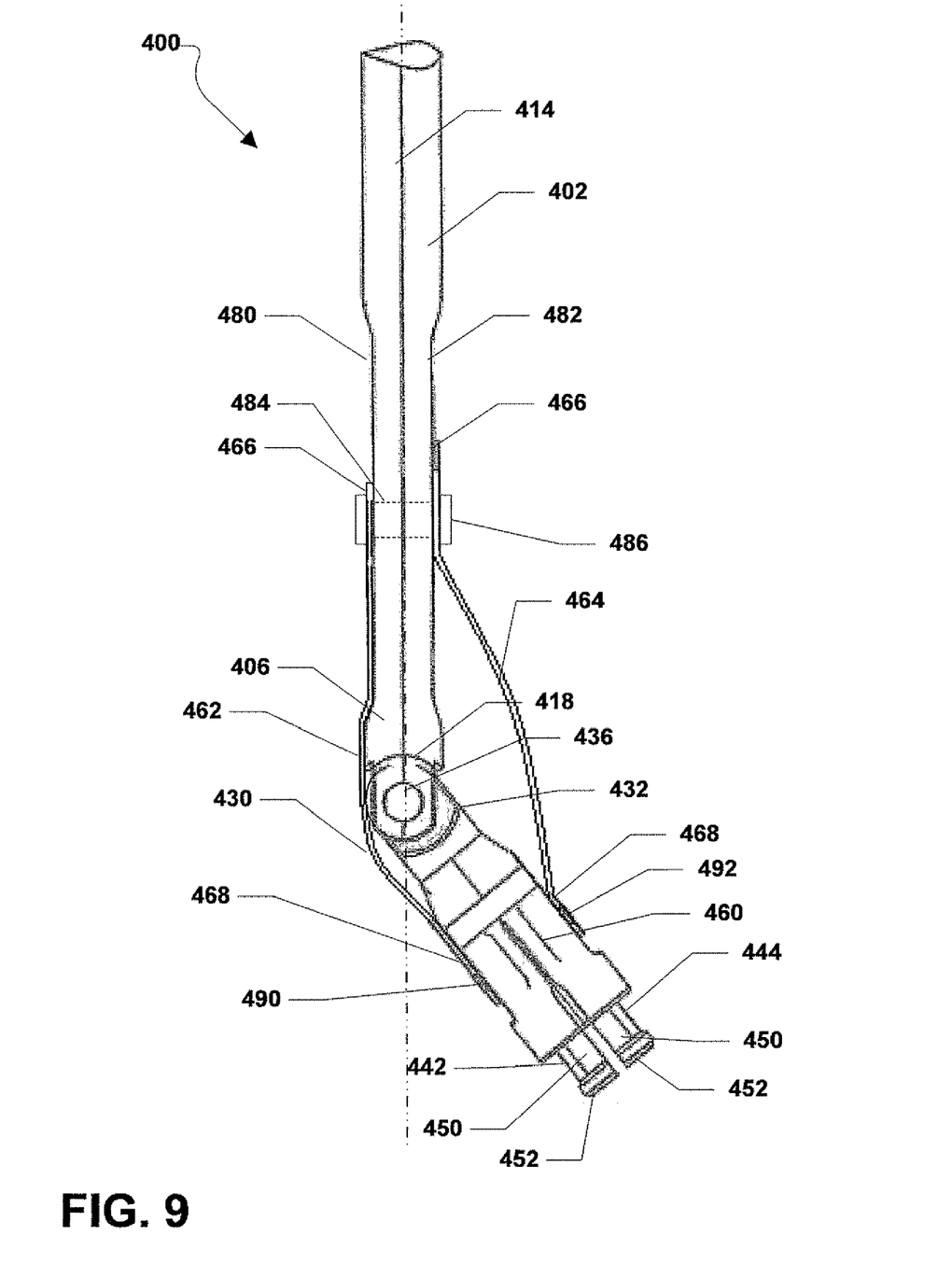
FIG. 9 is a detailed view of the surgical staple inserter without any elements removed.

FIG. 9 shows that the shaft 402 can be formed with a first spring engagement portion 480 and a second spring engagement portion 482 near the distal end 406 of the shaft 402. Each spring engagement portion 480, 482 can be substantially flat and can be configured to receive a portion of each spring 462, 464 there against. In particular, the proximal end 466 of the first spring 462 can be placed against the first spring engagement portion 480 and the proximal end 466 of the second spring 464 can be placed against the second spring engagement portion 482.

Figure 10:
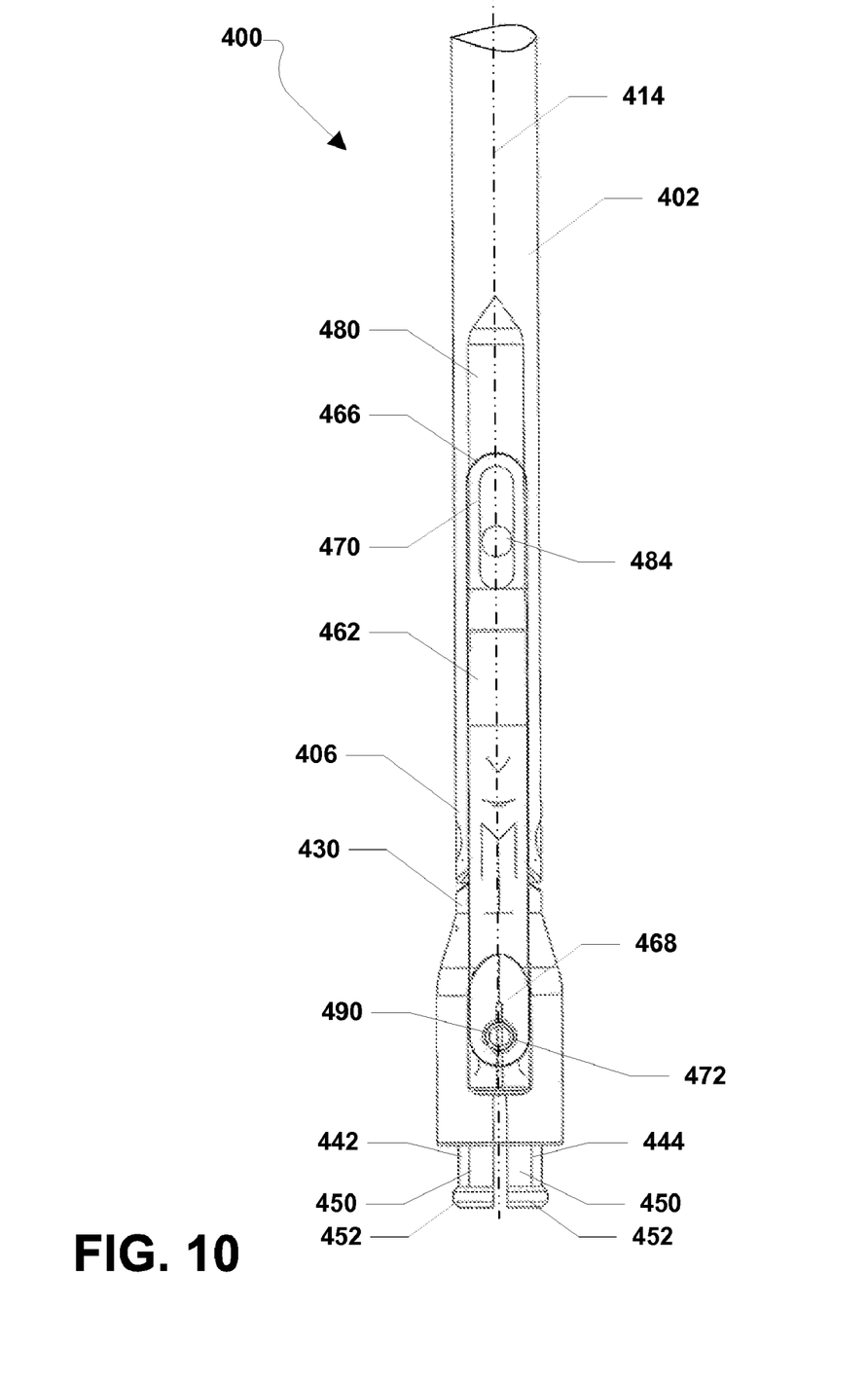
FIG. 10 is another detailed view of the surgical staple inserter without any elements removed.

As shown in FIG. 9 and FIG. 10, the shaft 402 can include a spring fastener hole 484 that can extend substantially perpendicular to longitudinal axis 414 of the surgical staple inserter 400 between the first spring engagement portion 480 and the second spring engagement portion 482. In a particular embodiment, as shown in FIG. 10, the slot 470 in each spring 462, 464 can be aligned with the spring fastener hole 484 formed in the shaft 402. Further, as shown in FIG. 9, a first spring fastener 486 can extend through the slot 470 in each spring 462, 464 and through the spring fastener hole 484 in the shaft 402. The first spring fastener 486 can maintain the proximal end 466 of each spring 462, 464 in close contact with a respective spring engagement portion 480, 482 of the shaft 402. Further, the first spring fastener 486 can allow each spring 462, 464 to slide linearly with respect to the shaft 402, e.g., as the staple engagement arm 430 rotates with respect to the shaft 402. The length of the slot 470 in each spring 462, 464 can limit the distance that each spring 462, 464 can move relative to the shaft 402.

As shown in FIG. 9, the distal end 468 of the first spring 462 can be attached to the sleeve 460 by a second spring fastener 490. Further, the distal end 468 of the second spring 464 can be attached to the sleeve 460 by a third spring fastener 492. In a particular embodiment, the spring fasteners 490, 492 can be threaded fasteners, e.g., bolts, screws, or other similar devices.

During use, the surgical staple inserter 400 can be moved between a straight position and a bent position. In the straight position, the staple engagement arm 430 can be substantially aligned with the shaft 402 of the surgical staple inserter 400. Specifically, a longitudinal axis of the staple engagement arm 430 can be substantially parallel to, or collinear with, a longitudinal axis of the shaft 402. Further, in a particular embodiment, in the straight position, the springs 462, 464 can be in a substantially relaxed state. Moreover, in another particular embodiment, in the straight position, the springs 462, 464 can provide a biasing force to maintain the staple engagement arm 430 substantially aligned with the shaft 402.

In the bent position, the staple engagement arm 430 can be rotated with respect to the shaft 402 of the surgical staple inserter 400. Further, in the bent position, one spring 462, 464 can bow outward, away from the shaft 402, and the other spring 462, 464 can bend with the staple engagement arm 430. Also, the springs 462, 464 can slide with respect to the shaft 402 as the staple engagement arm 430 is rotated with respect to the shaft 402. When a bending force is removed from the surgical staple inserter 400, the springs 472, 474 can return the surgical staple inserter 400 to the straight position.

In a particular embodiment, the staple engagement arm 430 can rotate with respect to the shaft 402 in a range of minus five degrees to plus five degrees (−5° to +5°). In another embodiment, the staple engagement arm 430 can rotate with respect to the shaft 402 in a range of minus ten degrees to plus ten degrees (−10° to +10°). In yet another embodiment, the staple engagement arm 430 can rotate with respect to the shaft 402 in a range of minus fifteen degrees to plus fifteen degrees (−15° to +15°). In still another embodiment, the staple engagement arm 430 can rotate with respect to the shaft 402 in a range of minus twenty degrees to plus twenty degrees (−20° to +20°). In yet still another embodiment, the staple engagement arm 430 can rotate with respect to the shaft 402 in a range of minus twenty-five degrees to plus twenty-five degrees (−25° to +25°).

In another embodiment, the staple engagement arm 430 can rotate with respect to the shaft 402 in a range of minus thirty degrees to plus thirty degrees (−30° to +30°). In yet another embodiment, the staple engagement arm 430 can rotate with respect to the shaft 402 in a range of minus thirty-five degrees to plus thirty-five degrees (−35° to +35°). In still another embodiment, the staple engagement arm 430 can rotate with respect to the shaft 402 in a range of minus forty degrees to plus forty degrees (−40° to +40°). In yet still another embodiment, the staple engagement arm 430 can rotate with respect to the shaft 402 in a range of minus forty-five degrees to plus forty-five degrees (−45° to +45°).

As described herein, the surgical staple inserter 400 includes a staple engagement arm 430 that rotates with respect to a shaft 402 around a single pivot point, e.g., a cylindrical element 436, in a single plane through the pivot point. In an alternative embodiment, a ball-and-socket joint can connect the staple engagement arm 430 to the shaft 402. For example, the shaft 402 can include a ball formed on the distal end 406 of the shaft 402 and the staple engagement arm 430 can include a socket that fits around the ball. Alternatively, the distal end 406 of the shaft 402 can be formed with a socket and the staple engagement arm 430 can include a ball that fits into the socket. The ball-and-socket joint can allow the staple engagement arm 430 to rotate with respect to the shaft around a single pivot point, but in many different planes through the ball-and-socket joint.

Description of a Method of Using a Surgical Staple Inserter

Figure 11:
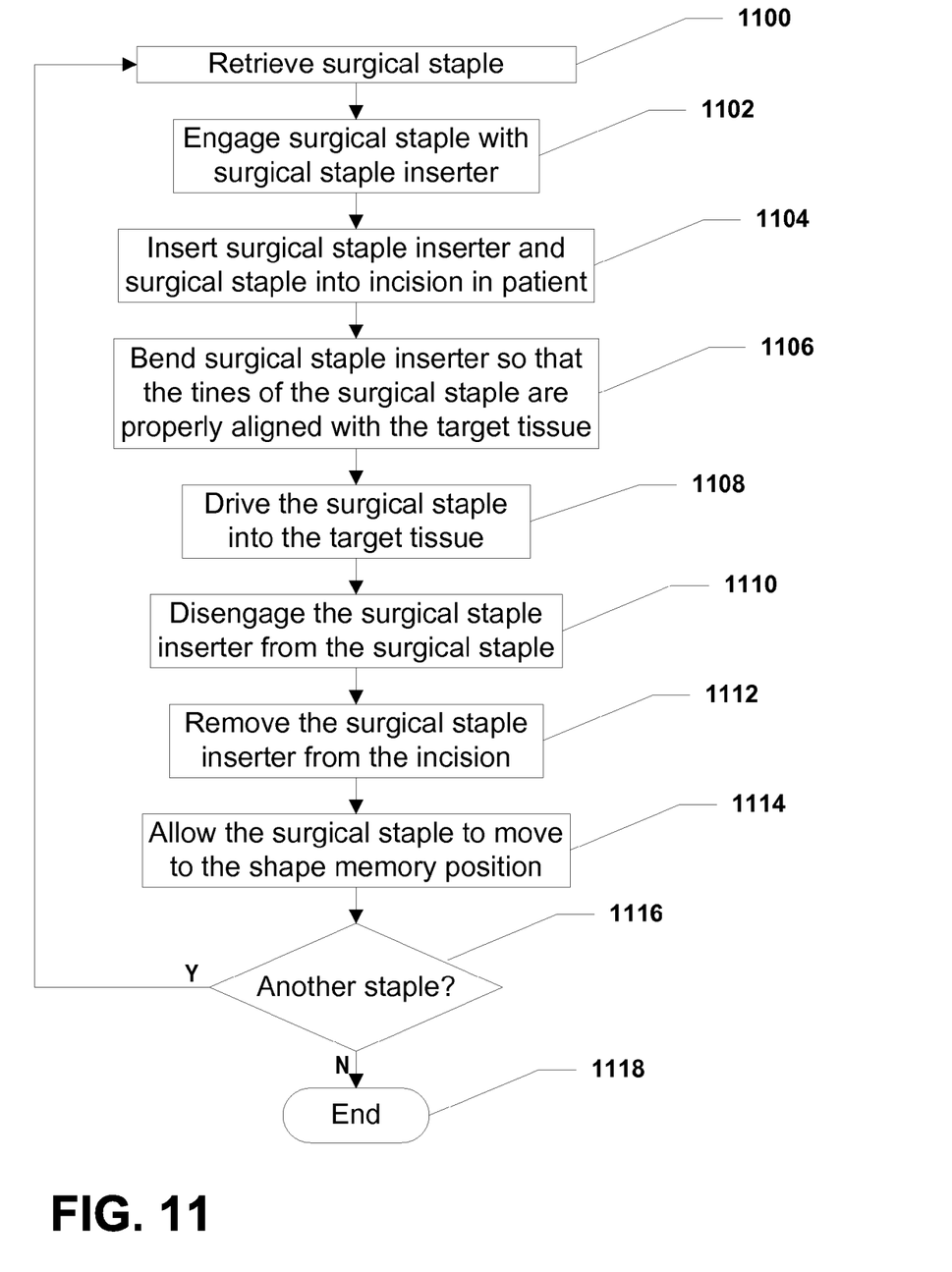
FIG. 11 is a flow chart illustrating one method of using a surgical staple inserter.

Referring to FIG. 11, a method of using a surgical staple inserter is shown. In a particular embodiment, the surgical staple inserter can be the surgical staple inserter shown and described herein. Further, in a particular embodiment, the surgical staple inserter can be used in conjunction with the surgical staple shown and described herein.

Commencing at block 1100, a surgical staple can be retrieved. At block 1102, the surgical staple can be engaged with the surgical staple inserter. Moving to block 1104, the surgical staple inserter and the surgical staple can be inserted into an incision in a patient. At block 1106, the surgical staple inserter can be bent in situ so that the tines of the surgical staple are properly aligned with the target tissue within the patient. Proper alignment can include both tines contacting the target tissue substantially at the same approach angle.

Proceeding to block 1108, the surgical staple can be driven into the target tissue. The surgical staple can be driven into the tissue manually by a surgeon using his or her hands. The target tissue can be flesh, bone, or a combination thereof. Further, the target tissue can be a vertebra. Also, the target tissue can be adjacent vertebra and the surgical staple can span the adjacent vertebra. At block 1110, the surgical staple inserter can be disengaged with the surgical staple. Further, at block 1112, the surgical staple inserter can be removed from the incision. Moving to block 1114, the surgical staple can be allowed to move to a shape memory position within the target tissue.

At decision step 1116, it can be determined whether another surgical staple is needed for the patient. If so, the method can return to block 1100 and continue as described herein. Otherwise, the method can end at state 1118.

CONCLUSION

With the configuration of structure described above, the surgical staple inserter provides a device that can be used to install surgical staples within a patient. One or more elements of the surgical staple inserter can allow the surgical staple inserter to be used to insert surgical staples in areas within a patient that may be difficult to access. Further, one or more elements of the surgical staple inserter can allow the surgical staple inserter to be used to properly align a surgical staple within target tissue regardless of the orientation of the handle of the surgical staple inserter relative to the target tissue. Moreover, one or more elements of the surgical staple inserter can allow the surgical staple inserter to properly align a surgical staple with respect to target tissue in areas that are difficult to access. Also, one or more elements of the surgical staple inserter can allow the surgical staple inserter to be used within an access device, e.g., a small space retractor, a tube, etc., that can be installed within a patient to provide access to the target area.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A surgical staple inserter, comprising:
    a shaft;
    a staple engagement arm pivotably attached to the shaft at a pivot point to permit a pivoting movement between the staple engagement arm and the shaft, wherein the staple engagement arm is configured to engage an inserter engagement hole in a surgical staple; and
    a first spring attached to the shaft and the staple engagement arm, wherein the first spring provides a biasing force to the pivoting movement between the shaft and staple engagement arm, and wherein the first spring comprises a slot for engaging a first spring fastener extending through the shaft, the first spring capable of sliding linearly with respect to a longitudinal axis of the shaft as the staple engagement arm pivots with respect to the shaft.

2. The surgical staple inserter of claim 1, further comprising:
    at least two fingers extending from the staple engagement arm, wherein each finger is configured to extend through the inserter engagement hole and splay radially outward in order to removably engage the inserter engagement hole.

3. The surgical staple inserter of claim 2, further comprising:
    a protuberance formed substantially near a distal end of each finger, wherein each protuberance is configured to engage the surgical staple adjacent to the inserter engagement hole and maintain the surgical staple on the surgical staple inserter.

4. The surgical staple inserter of claim 3, further comprising:
    a groove formed in the shaft; and
    a tongue formed in the staple engagement arm, wherein the tongue extends into the groove.

5. The surgical staple inserter of claim 4, further comprising:
    a cylindrical member extending through the groove and the tongue, wherein the staple engagement arm rotates with respect to the shaft around the cylindrical member.

6. The surgical staple inserter of claim 2, wherein the first spring is configured to maintain the staple engagement arm substantially aligned with the shaft when the first spring is relaxed.

7. The surgical staple inserter of claim 6, wherein as a bending force is applied to the staple engagement arm, the staple engagement arm rotates with respect to the shaft and the first spring bends.

8. The surgical staple inserter of claim 7, wherein the first spring returns the staple engagement arm to alignment with the shaft when the bending force is removed from the staple engagement arm.

9. A surgical staple inserter, comprising:
    a shaft;
    a staple engagement arm pivotably engaged with the shaft at a pivot point to permit pivoting movement between the shaft and staple engagement arm; and
    a spring connected to the shaft and the staple engagement arm, the spring configured to bias the pivoting movement between the shaft and the staple engagement arm, wherein the surgical staple inserter is movable between a straight position in which the staple engagement arm is substantially aligned with the shaft and a bent position in which the staple engagement arm is rotated with respect to the shaft, and wherein the spring is connected to the shaft via a first spring fastener extending through the shaft and a slot in the first spring, wherein the first spring is capable of sliding linearly with respect to a longitudinal axis of the shaft as the staple engagement arm pivots with respect to the shaft.

10. The surgical staple inserter of claim 9, wherein in the straight position the spring provides a biasing force to align the staple engagement arm with the shaft.

11. The surgical staple inserter of claim 9, wherein in the straight position the spring is substantially relaxed.

12. The surgical staple inserter of claim 11, wherein in the bent position the spring is bent.

13. The surgical staple inserter of claim 12, wherein the spring moves the surgical staple inserter from the bent position to the straight position when a bending force is removed from the surgical staple inserter.

14. The surgical staple inserter of claim 9, further comprising:
   at least two fingers extending from the staple engagement arm, wherein each finger is configured to splay radially outward to engage a surgical staple.

15. The surgical staple inserter of claim 14, further comprising:
   a protuberance formed substantially near a distal end of each finger, wherein each protuberance is configured to maintain the surgical staple on the fingers of the surgical staple inserter.

16. The surgical staple inserter of claim 9, wherein the staple engagement arm is rotatable with respect to the shaft in a range of at least minus five degrees to at least plus five degrees (−5° to +5°).

17. The surgical staple inserter of claim 9, wherein the staple engagement arm is rotatable with respect to the shaft in a range of at least minus forty-five degrees to at least plus forty-five degrees (−45° to +45°).

18. The surgical staple inserter of claim 1, further comprising a second spring attached to the shaft and the staple engagement arm, wherein the second spring provides a biasing force to the pivoting movement between the shaft and the staple engagement arm.

19. The surgical staple inserter of claim 18, wherein the biasing force of the second spring opposes the biasing force of the first spring.

20. The surgical staple inserter of claim 18, wherein the first spring is attached to a side of the shaft opposite the second spring.

21. The surgical staple inserter of claim 18, wherein the first spring and the second spring span the pivot point between the shaft and the staple engagement arm, and wherein the first spring and second spring are laterally displaced from a longitudinal axis of the shaft.

22. The surgical staple inserter of claim 21, wherein the second spring comprises a slot at a proximal end attached to the first spring fastener within the shaft, the second spring capable of sliding linearly with respect to a longitudinal axis of the shaft as the staple engagement arm pivots with respect to the shaft.

* * * * *